United States Patent [19]

Bergman et al.

[11] Patent Number: 4,613,574

[45] Date of Patent: Sep. 23, 1986

[54] IN VITRO TEST FOR OCULAR TOXIC PROPERTIES

[75] Inventors: Hyman C. Bergman, Los Angeles; James F. Godfrey, Venice; Virginia C. Gordon, Pacific Palisades, all of Calif.

[73] Assignee: Preventive Diagnostics Corporation, Carson, Calif.

[21] Appl. No.: 607,483

[22] Filed: May 4, 1984

[51] Int. Cl.[4] .................... G01N 21/75; G01N 33/50
[52] U.S. Cl. ........................................ 436/2; 436/164
[58] Field of Search ...................... 436/86, 87, 164, 2

[56] References Cited

PUBLICATIONS

Douglas et al, Chemical Abstracts, vol. 101, 1984, No. 101:67185m.
Burton et al, Chemical Abstracts, vol. 96, 1982, No. 96:1498n.
Mochizuki et al, Chemical Abstracts, vol. 99, 1983, No. 99:86100m.

*Primary Examiner*—Arnold Turk
*Attorney, Agent, or Firm*—Ciotti & Murashige

[57] ABSTRACT

A reagent and method for in vitro determination of the eye irritating properties of individual compounds and/or mixtures is disclosed. The material to be assessed is combined with the reagent which provides a response, for example, the production of a precipitate, which is proportional to the deleterious response elicited by the material in the human eye.

12 Claims, No Drawings

IN VITRO TEST FOR OCULAR TOXIC PROPERTIES

TECHNICAL FIELD

This invention relates to the field of testing materials for their capacity to irritate the human eye. More specifically, the invention relates to an in vitro test which can predict the ability of a specified material to cause temporary or permanent damage if placed in contact with the human eye.

BACKGROUND ART

In the United States and elsewhere in the technologically developed world, it is customary and often legally mandated, to assess the capacity of consumer products such as shampoos, detergents, cosmetics, or other materials which are likely to be handled by the general public without eye protection, to cause temporary or permanent damage to the human eye. Because of the sensitivity and criticality of ocular tissue, it is clearly desirable and necessary to provide adequate labeling in the case of mild and temporary eye irritants or even to restrict the commercialization of compositions which contain components extremely damaging to the eye. It is estimated that more than a million tests are performed annually in the United States to examine various cosmetic and household produts for their potential harmfulness to the human eye. As in any instance where large numbers of tests need to be performed to screen for a particular property, it is desirable to have a testing procedure which is rapid, inexpensive, and reliable. Certainly an in vitro test would be most desirable.

Such an in vitro test is not currently available for substances which might irritate the eye. The most commonly utilized current screening procedure is an in vivo one, the Draize rabbit-eye test (Draize, J. H., et al *J Pharmacol Exptl Therap* (1944) 82:377). The disadvantages of this test are legion. First, as it is an in vivo procedure it necessarily involves some degree of maltreatment of test animals, and considerable expense. Secondly, it is lengthy. The procedure consists of placing the substance to be tested into the eyes of 3-9 albino rabbits and scoring the degree of irritation on the conjunctiva, cornea, and iris after periods of 3-21 days. The scoring of the results is, of course, subjective to some degree. The individuality of the test animals makes the results inherently unreproducible. Many attempts have been made to refine and improve the Draize test and to minimize its disadvantages (see, for example, Batista, S. P., et al, *Soc Cosmet Chemists* (1965) 16:119; Kay, J. H., et al, *Am Perfumer Cosmetics* (1965) 80:61; Gaunt, I. F., et al, *J Soc Cosmet Chemists* (1964) 15:209). However, the inherent deficiencies of this testing approach make impossible the attainment of the objective of a cheap, reliable, reproducible and predictive test for eye irritating properties.

As in all animal tests, the correlation with effects of the materials in human subjects is imperfect; however, the Draize test has become sufficiently well recognized, that a more straightforward test which produces results identical to those of the Draize would represent an improvement in the state of the art, and correlation with Draize results can reasonably be used to evaluate such a test.

The clear desirability of an in vitro procedure has led a number of researchers to devise tests involving cell cultures as opposed to whole animals. For example, the method of Ferguson, T. F. M., et al, *Food and Cosmet Toxicol* (1974) 12:359 employs cultured mouse fibroblast cells and uses the ability of a material to inhibit the uptake of tritiated uridine by these cells as a measure of its eye irritation capacity. The method of Stark, L., et al, *Chemical Week* (1983) May 26:27 uses a procedure whereby mouse cell cultures are exposed to irritants, and the fluids from such cultures evaluated for their effect on the migration of macrophages. The method of Char Jumblatt, M., *Vision Res* (1981) 21:45 uses the level of plasminogen activator in rabbit corneal cells in culture as a measure of the eye-irritating capability of a substance. Finally, inhibition of culture growth in fibroblast or HeLa cells was used as a criterion by Litterst, C. L., et al, *Arch Environ Health* (1971) 22:454. Two additional methods employ mouse or rabbit ileum and assess, respectively, the penetration capacity of the substance to be tested (Muir, C. K., *Toxicology Letters* (1983) 19:309) and the response of a chorioallantroic membrane of chick embryos (Leighton, J., et al, *Proc of the Symposium, Product Safety Evaluation*, A. M. Goldberg, Editor, Mary Ann Liebert Publications, New York (1983)).

All of the foregoing in vitro methods require either living cells in tissue culture or isolated membranes in tissue culture. All suffer from the disadvantages of lack of reproducibility, lack of objectivity, and lack of perfect correlation with the property desired to be measured, as does the Draize method. While these procedures provide an alternative to the strictly in vivo approach of Draize, they do not achieve the simplicity and standardization one expects from testing based on chemical reagents which can be manufactured and stored, and reproduced exactly. The method of the present invention offers such a test. It provides a standard, quick, reproducible, objective measure of the capacity of any material to cause irritation in the human eye. It does not involve use of small animals, and does not require the expense of maintaining, caging, and feeding facilities for them.

DISCLOSURE OF THE INVENTION

The invention provides a reagent and a method for assessing the capacity of materials to cause temporary or permanent irritation in the human eye. The magnitude of the response given by the reagent test system of the invention correlates to the severity of the eye irritation which will be caused by the tested material. The reagent is a defined or semi-defined mixture of materials which has the advantages and properties of standard chemical reagents. The procedure is straightforward and rapid. The reagent and substance to be tested can be mixed and the result assessed visually without instrumentation, or can be quantitated, using a variety of laboratory instruments which are commonly available in analytical laboratories, if desired.

Accordingly, in one aspect, the invention relates to a reagent useful for predicting the toxicity of a material to the human eye wherein the reagent comprises a mixture of proteinaceous substances which are capable of quantitative response to the presence of an ocular irritant. In other aspects, the invention relates to methods of predicting the ocular toxicity of materials using the reagent of the invention and to test kits useful in performing such methods.

MODES OF CARRYING OUT THE INVENTION

A. Definitions

As used herein, "toxicity" of a material to the human eye or "ocular toxicity" refers to the ability of this material to cause negative responses in the human eye which take the form of either temporary or permanent damage to its tissues. This toxicity is evidenced by causing pain, opaqueness of the cornea or iris or both, congestion, swelling, hemorrhaging, or gross destruction of the iris, redness or dilation of the conjunctiva or production of discharge. Thus, the word "toxicity" or "toxic" in this context is defined broadly to include any discomfort or injury which results from the presence of a material in contact with the human (or other mammalian) eye.

"Clear aqueous liquid" refers to a liquid, usually a mixture, which is, in substantial part, water and which is functionally transparent to light in the visible range. "Functionally transparent to light in the visible range" means that sufficient light is transmitted by the sample to permit measurable absorbances to be detected upon precipitation of the components of the liquid. For example, even absorption of visible wavelengths in amounts of about 0.8 absorbance units in a 1 cm cuvette permits a readable range for additional absorbance caused by such precipitation. Of course, the permissible absorbance of such functionally transparent samples depends on the path length provided and upon the absorbance range measurable by the available instrument.

"Ocular irritant" refers to a substance which is capable of displaying toxicity to the human eye when placed in contact with it.

"Compatible" conditions of pH and/or ionic strength refers to ranges of these parameters which are consistent with the property of the reagent to precipitate only in the presence of an ocular irritant.

"Reagent" refers to the reaction mixture in contact with the sample to be tested; "preparation" refers to a material which, when diluted with solvent and sample results in the reagent.

B. General Description

B.1 General Parameters of the Testing Procedure

The present invention provides a reagent which, when mixed with a substance to be tested for ocular toxicity, produces a response which is measureable qualitatively or quantitatively in proportion to the ocular toxicity of the sample. The direct response of mixing the sample with the reagent is the formation of a precipitate, whose magnitude can be assessed using a variety of techniques which are described in detail below. The formation of the precipitate is, in a very rough sense, a mimetic response to that produced in the eye by the irritant. Therefore, the response of the reagent to the substance to be tested can be used as a predictor of the response of eye tissue to the same material.

B.2 The Reagent

The reagent is used in the form of a clear aqueous liquid which will be mixed with the substance to be tested. However, the active ingredients of the reagent mixtures of these substances can be prepared as solids, and when subsequently dissolved to form a clear aqueous liquid reagent, will precipitate or otherwise respond to the presence of an ocular irritant. Thus, the mixture of components in the desired amounts can be supplied not only already dissolved to form the finished reagent, but also in solid form either as a powder, lyophilized solid, or a gel, which can be subsequently reconstituted to form the reagent.

In any case, the reagent is preferably supplied in a somewhat more concentrated form than the final concentration of components desired, so that it can be added to a reaction mixture with a diluent and with the sample to be tested.

The mixture itself is a composition of proteinaceous materials, amino acids, carbohydrates, and ionic compounds which, in some sense, mimics the response of human eye tissue to contact with materials to be tested.

The clear aqueous liquid reagent of the invention contains solutes or colloidal particles which will remain in solution or in a colloidal state until a ocular irritant is added, whereupon precipitation occurs. To achieve this, the reagent contains at least one precipitant and at least one stabilizer, and is maintained at compatible pH and ionic strength conditions. It is preferable to include at least one enhancer, and to protect the reagent against deterioration by supplying antibodies and enzyme inhibitors.

Precipitants represent the desired response of the reagent to an ocular irritant—i.e. these materials precipitate to give turbidity or a separable solid from the mixture. Effective precipitants include the globular proteins, which are best employed as mixtures of several different globulins such as globulin $G_1$, $G_2$ and $G_3$ or subcombinations thereof. A single globulin is operable, though not as sensitive. The total globulin concentration in the finished reagent is in the range of 0.001–10%, preferably 0.01–5%, depending on the class of globulins used. Alternate precipitants suitable for the reagent of the invention include, for example, macroglobulins, certain glycosaminoglycans, and mucoproteins.

(In the above paragraph, and in those following, the concentration ranges are given as wt/volume percentages (unless otherwise specifically indicated), and reference the volume of finished reagent. In typical preparations, the concentration will be 5–10 times higher, so as to permit dilution as outlined above.)

Stabilizers prevent premature aggregation of the precipitant and may make the extent and form of the aggregation more reproducible. Suitable stabilizers include, for example, amino acids, such as glycine, glutamine, valine, leucine and the like, peptides of 200–5000 daltons and non-globulin proteins such as albumins. A wide range of concentrations and of combinations of stabilizers is workable. In one preferred embodiment, glycine may be used as the only stabilizer in the concentration range about 0.005–0.5%. In general, total stabilizer concentration is in the range of 0.001%–10%, preferably 0.1%–5% depending on the nature of the stabilizer chosen.

Compatible pH range and ionic strength may be maintained by adjusting the buffering capacity and ionic status of the foregoing two required components—i.e. precipitant(s) and stabilizer(s) or, preferably are obtained by providing suitable ionic compounds or buffers. A compatible pH range is between about 1–10, but preferably between about 2–9. Higher pH values denature the precipitant and allow it to remain in solution, even in the presence of ocular irritants, lower pH values may cause premature precipitation. Suitable buffers in this range include phosphate salts, acetate salts, Tris-Cl, bicarbonate and a variety of other compounds known in the art. Ionic strength can vary over a wide range from about 0.05 M to 0.5 M, and is generally high enough to be workable (due to the presence of charged moieties in the precipitant and stabilizer) even in the absence of additional salts. However, this parameter can be increased, if desired, by the addition of such commonly available salts as NaCl, KCl, or NaNO$_3$.

It is desirable, though not absolutely necessary, to include in the reagent enhancers which interact with the molecules of precipitant so as to increase its aggregation in the presence of ocular irritants. Such enhancers are, most typically, glycoproteins such as ovomucoids, mucopolysaccharides; mucin and carbohydrates such as glucose; and lipids, such as phospholipids. The desired concentration range varies, of course, with the nature of the enhancer but is generally in the range of 0–10%.

The reagent may be further protected from deterioration by addition of bacteriostats or bacteriocides such as sodium azide, and by use of enzyme inhibitors, such as N-ethylmaleimide.

In the foregoing paragraphs, applicants have set forth the parameters required to constitute the reagent as a defined medium using predetermined amounts of available substances. However, it is also possible to achieve the result of a workable reagent, containing the proper concentrations of precipitant and stabilizers, and, indeed, suitable amounts of optional components such as enhancer by utilizing extracts of natural materials which contain, for example, globulins, peptides, albumin, and other desired components of the reagent. Two natural materials which are particularly preferred to provide such extracts are egg whites, jack beans and other legumes and combinations, thereof all of which contain globulins. The preparations can be made using water or salt solutions as a diluent, however, they are preferably made using an extracting solution containing, for example, ionic compounds and buffers, and/or supplementary components such as EDTA to adjust the concentrations of ions which affect the precipitant. The extracting solution, if such natural materials are used, may not need to contain precipitants or stabilizers, as these are found in the natural materials themselves.

B.3 The Method

A major virtue of the method of the invention is its simplicity. The crux of the procedure is merely contacting the reagent of the invention with the material to be tested. The results can be made quantitative either by quantitative measurement of the amount of precipitate directly, by indirect measurement of the amount of precipitate by, for example, colorimetric means, or by ascertaining the presence or absence of a preset quantitative response using serial dilutions of sample in admixture with the reagent.

The mass of the precipitate can be obtained by separation from the mixture, e.g., by centrifugation, drying and weighing. However, more preferred is measurement of turbidity, which method is more rapid and less subject to complications due to physical variation of the precipitate during drying. The amount of turbidity formed can be measured using standard absorbance readings obtained with spectrophotometers or colorimeters. It is important to use both the reagent and sample as "blank"s in such procedures, as some light absorbance or scattering will be caused by the presence of macromolecular species in the reagent itself or by the sample. In some samples, the total absorbance contributed by the sample and reagent separately may be on the order of 0.8 OD units or more per cm path length, so that it may be desirable to decrease the path length if absorbance measurements are used, or to employ a dedicated instrument calibrated to a higher absorbance range. Of course, the absorbance of both the sample and reagent blank are subtracted from that of the test sample. Light scattering due to turbidity can best be quantitated at 340 nm or 430 nm. Resolution to a narrow wavelength band is unnecessary.

In the alternative, nephelometry may be substituted for absorbance readings, and, indeed, may be preferred in some cases. This method of quantitation is, in general more sensitive and covers a larger range of concentrations than absorbance measurements. However, due to the ubiquitous use of colorimetry, this method is preferred for most commercial applications.

The amount of precipitate may also be quantitated by measuring the amount of protein. The precipitant is separated from the mixture by, for example, centrifugation and removal of the supernatant, and the isolated precipitate subjected to standard techniques for protein determination known in the art, such as the buiret method, the method of Lowry (Lowry, O. H. et al, *J Biol Chem* (1957) 195:265) or by separation on polyacrylamide gel and staining a diagnostic band or bands with Coomassie blue or silver stain.

Alternatively, the amount of precipitate can be assessed quantitatively by attaching a label to a component of the reagent so that the quantity of material carried down with the precipitate can be assessed by the quantity of label present in the precipitate or remaining in the supernatant. The label may be, for example, a radioactive material, a chromophore, or a fluorophore. In any case, the supernatant and precipitate are separated, and the amount of label read in the desired fraction by means appropriate to the nature of the label.

If the label in the precipitate is quantitated, the amount present is a direct measure of the ocular toxicity of the sample; if the label is quantitated in the supernatant, the amount is inversely proportional to the toxicity.

The proteinaceous precipitate can readily be labeled by a variety of means employing such commonly available $\beta$-emitting radioisotopes as $^{14}C$ and $^{3}H$. The activity in the precipitate can then be determined by use of a Geiger counter, or that in the supernatant using scintillation counting. Other isotopes such as $^{125}I$ or $^{131}I$ can also be conjugated to the protein precipitant and counted using similar techniques.

Conjugated chromophores and fluorophores are most conveniently determined in the supernatant fraction, although they may also be solubilized from the separated precipitate and measured. Convenient fluorophores include dansyl, fluorescein and rhodamine dyes. Convenient chromophores include for example p-nitroaniline, which absorbs at 405 nm.

The label may also be a substrate for an enzyme catalyzed reaction which can be quantitated using standard means. For example, any of the substrates of the peroxidase reaction could be used as label, and the enzyme added to the supernatant fraction after separation of the precipitate to assess the concentration of substrate remaining.

B.4 Evaluation of Results

As set forth above, it would be desireable to have a perfect correlation between the results of the test as performed by the method of invention and the capacity of a material to irritate the human eye. However, the results of human experience with respect to the large number of irritants for which testing is desireable are not readily available in retrieveable form. The results of Draize testing on large numbers of substances is. Therefore, a threshold criterion for predictive validity of the testing procedures of the invention is correlation of its results with those of Draize testing on the same substances.

Accordingly, calibration curves have been prepared which show the relationship between the absorbance readings obtained using 340 nm in assessing the turbidity caused by the test substances in the method of the present invention with the results of the Draize test. Similar procedures may be used to calibrate other primary results criteria such as absorbance at other wavelengths, nephelometric readings, absorption due to color reagents, and radioactivity.

Typically, it is found that 340 nm absorbance follows a linear pattern with increasing concentration of test substance but plateaus at a level characteristic of each individual material. This is expected behavior in absorbance measurements, and therefore, it is possible to establish the position on the absorbance curve being read for each material tested. Using those data, testing can be done in the range of linearity for a particular material, thus assuring that the readings for that material will fit into the general calibration curve for the test method.

Once each substance to be tested is shown to be generating readings in the linear range, by verifying the readings for, e.g., sample sizes of 100 $\mu$l, 200 $\mu$l, and 500 $\mu$l in a 1 ml total volume, the absorbances obtained at these sample sizes can be classified so as to correlate with the Draize results test ranges. A more detailed explanation of the specific correlations established using 340 nm absorption as the primary test criterion is given in ¶ C.2.b.

C. Examples

The following examples are intended to illustrate but not to limit the invention.

C.1 Preparation of Reagent Mixture

The following are prepared by using a buffer solution in some cases containing plant or animal globulins to extract either egg white or jack bean powder or both. If egg white is used, the separated whites are diluted with the buffer using 1 ml egg white per 2 ml buffer. If jack bean powder is used, 2 g finely powdered bean is soaked in 100 ml extraction buffer for 2 hours, and filtered twice with Whatman #40 paper to remove residue.

Preparations A–C are the concentrations of components shown in preparations which are typically diluted 2–10 times for the finished reagent concentration desired.

Preparation A

The first 16 components derive from the extraction buffer, the last 6 from jack beam powder.

| Compound | Concentration |
| --- | --- |
| $CaCl_2$ | 0.02% |
| KCl | 0.04% |
| $MgSO_4$ | 0.01% |
| $NaH_2PO_4:H_2O$ | 0.01% |
| NaCl | 0.2 M |
| isoleucine | 0.002% |
| glutamine | 0.03% |
| leucine | 0.002% |
| lysine:HCl | 0.004% |
| tyrosine | 0.002% |
| valine | 0.002% |
| NaOAc | 0.1 M |
| EDTA | 0.1% |
| N—ethylmaleimide | 0.01% |
| $NaN_3$ | 0.02% |
| glucose | 0.1% |
| globulin $G_1$ | 0.1–0.2% |
| Mucopolysaccharide | 0.1–0.15% |
| albumin | 0.1–0.3% |
| carbohydrates | 0.2–0.3% |
| lipids | 0.3–0.5% |
| saponins | 0.001–0.01% |

Preparation B

The first 14 components derive from extraction buffer, the remaining 9 from egg white.

| Compound | Concentration |
| --- | --- |
| NaOAc | 0.07 M |
| NaCl | 0.15 M |
| EDTA | 0.07% |
| N—ethylmaleimide | 0.07% |
| $NaN_3$ | 0.015% |
| $CaCl_2$ | 0.014% |
| KCl | 0.028% |
| $MgSO_4$ | 0.007% |
| $NaH_2PO_4:H_2O$ | 0.007% |
| lysine:HCl | 0.007% |
| isoleucene | 0.001% |
| tyrosine | 0.001% |
| glutamine | 0.021% |
| valine | 0.001% |
| conalbumin | 3% |
| ovalbumin | 22% |
| lipids | 0.4% |
| carbohydrates | 0.3% |
| ovomucoid | 4% |
| globulin $G_1$ | 0.5–1% |
| globulin $G_2$ | 0.5–2% |
| globulin $G_3$ | 0.2–2% |
| glucose | 0.1% |

Preparation C

The first 16 components derive from extraction buffer, the last 10 from egg white and jack bean powder.

| Compound | Concentration |
| --- | --- |
| $CaCl_2$ | 0.02% |
| KCl | 0.04% |
| $MgSO_4$ | 0.01% |
| $NaH_2PO_4:H_2O$ | 0.01% |
| NaCl | 0.15 M |
| isoleucine | 0.001% |
| glutamine | 0.02% |
| leucine | 0.001% |
| lysine:HCl | 0.002% |
| tyrosine | 0.001% |
| valine | 0.001% |
| NaOAc | 0.8 M |
| EDTA | 0.05% |
| N—ethylmaleimide | 0.1% |
| $NaN_3$ | 0.02% |
| glucose | 0.1% |
| globulin $G_1$ | 1–2% |
| globulin $G_2$ | 1–3% |
| globulin $G_3$ | 1–4% |

| Compound | Concentration |
| --- | --- |
| conalbumin | 2% |
| ovalbumin | 5% |
| ovomucoid | 2% |
| mucin | 1% |
| saponins | 0.10% |
| lipids | 0.5% |
| carbohydrates | 0.5% |

C.2. Results

C.2.a Preliminary Tests

In one protocol, 200 μl of preparation A were used in a total volume of 1 ml. Serial sample amounts of 500 μl, 250 μl, 100 μl and 50 μl were used, and optical density at 340 nm was read in a Beckman DV-8B spectrophotometer. The resulting absorbance was used as a criterion for ocular toxicity. Absorbances above about 1.0 OD unit were considered indicative of ocular toxicity.

The results were placed in broad categories of:
- non-irritant (N) <1.0
- mild irritant (Mi) 1.0–2.0
- moderate irritant (Mo) 2.0–2.5
- severe irritant (S) >2.5

The results in Table 1 below show absorbance values for 500 μl sample size and the categorization of results using the arbitrary absorbance range criteria indicated. The categories are compared with those reported in standard tests as indicated. (The concentrations given in column 1 refer to the concentration of the sample in the 500 μl portion as added to the reagent mixture.)

TABLE 1

| Concentration/Sample | OD$_{340}$ | Class | Invivo Draize Test Results |
| --- | --- | --- | --- |
| baby shampoo/100% | 0.63 | N | N (1) |
| methyl paraben/0.2% | 0.75 | N | N (1) |
| benzalkoniumchloride/1% | 2.51 | Mo—S | |
| benzalkoniumchloride/0.5% | 2.43 | Mo—S | Mo—S (4) |
| benzalkoniumchloride/0.1% | 2.43 | Mo—S | Mo (2) |
| resorcinol/100% | 2.52 | Mo | Mo (4) |
| resorcinol/5% | 0.40 | N | N (4) |
| sodium lauryl sulfate/40% | 1.00 | Mi | Mo—S (2) |
| propylene glycol/25% | 0.74 | N | N—Mi (3) |
| thimerosal/2% | 0.69 | N | Mi (4) |
| thimerosal/0.5% | 0.002 | N | N (4) |

(1) Applied Biological Sciences, Glendale, CA.
(2) Griffith, J. F., et al, Tox and Appl Pharmacol (1980) 55:501.
(3) Conquet, T. H., et al, Tox and Appl Pharmacol (1977) 39:129.
(4) Burstein, N. L., Survey of Opthamol (1980) 25:15.

C.2.b Results of Calibrated Study

The preliminary results obtained in ¶ C.2.a were further expanded by preparing correlation standards against Draize eye test results.

First, an arbitrary scale of classifications corresponding to the conventional use Draize classification was devised as set forth below.

| Rating | Scale | Draize Scale |
| --- | --- | --- |
| N | 1.0 | 0 |
| N—Mi | 1.5 | 1–10 |
| Mi | 2.0 | 10–20 |
| Mi—Mo | 2.5 | 20–40 |
| Mo | 3.0 | 40–60 |
| Mo—S | 3.5 | 60–80 |
| S | 4.0 | 80–110 |

Thus, for example, a test substance which received an average absorbance based scale rating of 3.5 would be classed as Mo-S; one which had an average scale value of 2.0 would be classed Mi.

The classification average was obtained by averaging the class obtained at 3 levels of sample volume, 50 μl, 100 μl, and 200 μl in a 1 ml reaction mixture averaging these classes and rounding to the next highest. The class obtained for each sample volume was determined according to the scale set forth as follows.

| Class | 1.0 | 1.5 | 2.0 | 2.5 | 3.0 | 3.5 | 4.0 |
| --- | --- | --- | --- | --- | --- | --- | --- |
| 50 μl | 0–0.4 | 0.4–0.8 | 0.8–1.2 | 1.2–2.0 | 2.0–2.5 | 2.5–3.0 | 3.0–3.5 |
| 100 μl | 0.4–0.8 | 0.8–1.2 | 1.2–2.0 | 2.0–2.5 | 2.5–3.0 | 3.0–3.5 | >3.5 |
| 200 μl | 0.8–1.2 | 1.2–2.0 | 2.0–2.5 | 2.5–3.0 | 3.0–3.5 | >3.5 | >3.5 |

Using these classes, the following results were obtained:

| | | 50 μl | 100 μl | 200 μl | Ave | Class |
| --- | --- | --- | --- | --- | --- | --- |
| 5% thimerosal | abs: | 0.21 | .29 | .43 | | |
| | scale: | 1.0 | 1.0 | 1.0 | 1.0 | N |
| 0.05% benzal- | abs: | 0.40 | 0.80 | 1.25 | | |
| koniumchloride | scale: | 1.5 | 1.5 | 1.5 | 1.5 | N—Mi |
| 70% Isopropanol | abs: | 0.93 | 1.42 | 1.85 | | |
| | scale: | 2.0 | 2.0 | 1.5 | 2.0 | Mi |
| 0.5% benzal- | abs: | 2.1 | 3.0 | 3.2 | | |
| koniumchloride | scale: | 3.0 | 3.0 | 3.0 | 3.0 | Mo |

C.2.c Comparison of Draize and Invention Method

Table 2 shows a comparison of results in the reagent of the invention using the calibrated system of ¶ C.2.b, the Draize rabbit eye test and general human experience. The results of the Draize test and their comparison to human experience was reported by Griffith, J. F., et al, Tox & Appl Pharmacol (1980) 55:501.

| | Human Experience | Draize Eye Test | Preparation A |
| --- | --- | --- | --- |
| Benzalkonium/chloride/0.1% | Mi—Mo | Mo | Mo—S |
| Acetic acid/3% | Mi—Mo | Mo | Mi—Mo |
| Sodium lauryl/sulfate/10% | N | Mo | N |
| Sodium lauryl/sulfate/29% | Mi | Mo | Mi |
| NaClO$_2$ | Mi | Mo | Mi |
| Formaldehyde/38% | Mi | S* | (Inhibitor) |
| Isopropanol/70% | Mi | Mo | Mo |

*very severe

In addition, 45 samples of household chemicals and common laboratory compounds, such as Ivory Liquid ®, Tide ®, acetone, sodium borate, cetalkonium chloride, thimerosal, and Chlorox ®, were tested using visual evaluation of results obtained when 500μ of test sample were added to 500μl of Preparation B, above. Results were compared with those of the standard Draize test as reported in the literature, according to the classification noted above. The results were substantially identical in 35 of these trials. In another six cases, the only difference was in the classification found, e.g., Mo in one test, S in the other. In only five cases was there a discrepancy in toxicity being indicated in one test and not in the other. DMSO, Selsun blue and Prell ® showed moderate toxicity in the test of the invention, but were non-irritating in the Draize tests performed by Applied Biological Sciences. Ajax ® gave a non-toxic result in the test of the invention, but was moderately toxic in the Draize test.

The results in Table 2 show that the correlation of the results obtained by the method of the invention correlate with human experience approximately as well as those obtained from the more laborious, expensive, and non-quantitative Draize test.

In summary, the invention provides a convenient, inexpensive screening procedure for obtaining preliminary data with respect to ocular toxicity of a material. Results are obtained with comparable reliability to those obtained from the relatively non-quantitative non-reproducible and expensive procedures, involving whole animals or from alternative, more complex, in vitro tests.

I claim:

1. A method for determining the toxicity of a material to the human eye, which method comprises:
   (a) contacting said material with a reagent which comprises:
      at least one precipitant in a concentration effective in precipitating in the presence of an ocular irritant; and
      at least one stabilizer in a concentration effective in preventing precipitation of the precipitant in the absence of an ocular irritant;
   in admixture with an aqueous medium to provide a clear aqueous liquid of compatible pH and ionic strength; and
   (b) measuring the amount of precipitate formed; and
   (c) comparing this amount with the amount of precipitate obtained using comparable amounts of a substance known to cause eye irritation.

2. The method of claim 1 wherein the reagent further includes an enhancer.

3. The method of claim 1 wherein the precipitant and stabilizer are in solid form and are dissolved in the aqueous medium to form the admixture.

4. The method of claim 1 wherein the reagent has a pH between 2 and 9 and an ionic strength of about 0.05 to about 0.5 M.

5. The method of claim 1 wherein the substance known to irritate the human eye is benzalkonium chloride.

6. The method of claim 1 wherein the amount of precipitate formed has been precalibrated by comparing the amount of precipitate formed with a series of substances with the response of the same substances in a Draize eye test.

7. The method of claim 1 wherein the relation of the amount of precipitate formed to ocular irritation has been calibrated by comparing the amount of precipitate measured with the optical densities of a series of portions of the reagent contacted with a series of concentrations of test substance, measured at 340 nm.

8. The method of claim 1 wherein the stabilizer is selected from the group consisting of amino acids, peptides, albumin, and mixtures thereof.

9. The reagent of claim 8 wherein the concentration of stabilizer is between 0.001% and 10% of the reagent.

10. The method of claim 1 wherein the precipitant includes at least one globulin protein.

11. The reagent of claim 10 wherein the globulin protein is selected from the group consisting of globulin $G_1$, globulin $G_2$, globulin $G_3$, and mixtures thereof.

12. The method of claim 11 wherein the concentration of globulin protein is between 0.001% and 10% of the reagent.

* * * * *